United States Patent
Yea et al.

(10) Patent No.: US 9,099,211 B2
(45) Date of Patent: Aug. 4, 2015

(54) PROMPT GAMMA-RAY DETECTION APPARATUS FOR ANALYZING CHEMICAL MATERIALS USING FEMTOSECOND PULSE LASER-INDUCED NEUTRONS

(75) Inventors: Kwon-Hae Yea, Seoul (KR); HyungKi Cha, Daejeon (KR); Sung-Man Lee, Daegu (KR); Sang-Soon Park, Chungcheongbuk-do (KR); Seong Hee Park, Daejeon (KR)

(73) Assignee: Korea Atomic Energy Research Institute, Daejeon (KR)

( * ) Notice: Subject to any disclaimer, the term of this patent is extended or adjusted under 35 U.S.C. 154(b) by 668 days.

(21) Appl. No.: 13/325,322

(22) Filed: Dec. 14, 2011

(65) Prior Publication Data

US 2012/0183111 A1     Jul. 19, 2012

(30) Foreign Application Priority Data

Dec. 20, 2010 (KR) .................. 10-2010-0130687

(51) Int. Cl.
  *G21G 1/06* (2006.01)
  *G01N 23/222* (2006.01)
(52) U.S. Cl.
  CPC ............ *G21G 1/06* (2013.01); *G01N 23/222* (2013.01); *G01N 2223/204* (2013.01)
(58) Field of Classification Search
  USPC ........................................ 376/106, 107, 122
  See application file for complete search history.

(56) References Cited

U.S. PATENT DOCUMENTS

| | | | |
|---|---|---|---|
| 4,682,043 A * | 7/1987 | Marshall | ............. 250/358.1 |
| 5,539,788 A | 7/1996 | Ruddy et al. | |
| 5,781,602 A | 7/1998 | Fero et al. | |
| 7,027,555 B2 * | 4/2006 | Proctor | ............. 378/57 |
| 2003/0161431 A1 | 8/2003 | Akers | |
| 2005/0077471 A1 * | 4/2005 | Edwards et al. | ............. 250/360.1 |

FOREIGN PATENT DOCUMENTS

| | | |
|---|---|---|
| JP | 07167803 A | 7/1995 |
| JP | 2005114386 A | 4/2005 |
| JP | 2008089610 A | 4/2008 |
| JP | 2009175065 A | 8/2009 |
| JP | 2009261634 A | 11/2009 |
| JP | 2010032451 A | 2/2010 |

(Continued)

OTHER PUBLICATIONS

Jeong et al., "Generation of High Energy Particles and Radiation form a Relativistic Plasma for Nuclear Research."*

(Continued)

*Primary Examiner* — Jack W Keith
*Assistant Examiner* — Sean P Burke
(74) *Attorney, Agent, or Firm* — Fredrikson & Byron, P.A.

(57) ABSTRACT

Disclosed herein is a prompt gamma-ray detection apparatus for analyzing chemical materials using femtosecond pulse laser-induced neutrons, which can be effectively used in the nondestructive inspection of various materials, such as metals, coal, cement, radioactive materials and the like as well as explosives and chemical materials, and which can provide better measurement results for the analysis of basic materials, and a method of measuring prompt gamma-rays using the apparatus. The prompt gamma-ray detection apparatus is advantageous because it can non-destructively analyze the elements in a chemical sample using a femtosecond pulse laser-induced neutron generator that solves the problems of an atomic reactor for research or a radioactive isotope as a neutron radiation source.

6 Claims, 2 Drawing Sheets

(56) References Cited

FOREIGN PATENT DOCUMENTS

| KR | 20060070898 A | 6/2006 |
|---|---|---|
| KR | 100783506 B1 | 12/2007 |

OTHER PUBLICATIONS

Lee et al., "Effect of the Prepulse Width on the Neutron Generation in a Femtosecond, Deuterated, Polystyrene Plasma."*

Kwon, et al., "Generation of laser-induced fast neutron and its application", KAERI/RR-3106/2009, 2010, 167 pgs.

Establishment of Nuclear Data for Future Nuclear R&D, GOVP1200718861, KAERI/RR-2744/2006, Jun. 29, 2007, 4 pgs.

Park et al., Development of Neutron Induced Prompt x-ray Spectroscopy System Using 252Cf, Analytical Science & Technology, vol. 16, No. 1, 12-24, 2003, © NuriMedia Co., Ltd., 2005, 13 pgs.

* cited by examiner

PROMPT GAMMA-RAY DETECTION APPARATUS FOR ANALYZING CHEMICAL MATERIALS USING FEMTOSECOND PULSE LASER-INDUCED NEUTRONS

CROSS-REFERENCES TO RELATED APPLICATION

This patent application claims the benefit of priority from Korean Patent Application No. 10-2010-0130687, filed on Dec. 20, 2010, the contents of which are incorporated herein by reference.

BACKGROUND OF THE INVENTION

1. Technical Field

The present invention relates to a technology for measuring explosives and chemical weapons using high energy laser-induced deuterium neutrons, and, more particularly, to a prompt gamma-ray detection apparatus for analyzing chemical materials using femtosecond pulse laser-induced neutrons, which can be effectively used in the nondestructive inspection of various materials, such as metals, coal, cement, radioactive materials and the like as well as explosives and chemical materials, and which can provide better measurement results for analysis of basic materials, and to a method of measuring prompt gamma-rays using the apparatus.

2. Description of the Related Art

Generally, it is known that a laser-induced neutron generator produces high-energy radioactive rays and fast neutrons by the interaction between high-energy femtosecond pulse lasers and deuterium.

Further, conventionally, Prompt Gamma-ray Neutron Activation Analysis (PGNAA) has been known as a technology of detecting nuclear reaction products by converting fast neutrons (~2.5 MeV) generated by the D-D nuclear reaction of a neutron generator into thermal neutrons.

As a conventional example of such prompt gamma-ray neutron activation analysis, Korean Patent registration No 10-0935801 (2009.12.29) discloses "a prompt gamma-ray detection system and a discrimination level determination method for detecting prompt gamma-rays using the same".

That is, the "prompt gamma-ray detection system and discrimination level determination method for detecting prompt gamma-rays using the same" disclosed in the Korean Patent registration No 10-0935801 intends to solve the problem of it being difficult for a conventional prompt gamma-ray detection system to accurately detect a sudden drop in radiation because the background attributable to neutrons is excessively high and to solve the problem of it being difficult to practically use a conventional prompt gamma-ray detection system in clinical radiation treatment although it can be generally used in proton beam measurement because the size of a neutron shielding material is excessively large.

Further, in order to solve the above problems, it is required to develop an optimized discrimination level determination method which can effectively measure prompt gamma-rays and simultaneously can reduce the influence of background gamma-rays by analyzing the energy spectrum of the measured gamma rays instead of decreasing the radiation of background gamma-rays using a shielding material. Therefore, the Korean Patent registration No 10-0935801 intends to provide a prompt gamma-ray detection system that can accurately measure a sudden drop in radiation based on the discrimination level at which the influence of background gamma-rays can be minimized and at which prompt gamma-rays can be effectively measured, and a discrimination level determination method for detecting prompt gamma-rays using the same.

In order to accomplish the above purpose, the prompt gamma-ray detection system of the Korean Patent registration No 10-0935801 comprises: a case including a first region, a second region and a rectangular through-hole penetrating one side of the first region and the other side of the second region; a deceleration unit disposed in the first region and made of paraffin; an absorption unit disposed in the second region and made of boron carbide; a shielding unit disposed in the absorption unit and made of lead; and a measurement unit detecting prompt gamma-rays that have passed through the through-hole and measuring the amount of radiation thereof.

Further, as another conventional example of such prompt gamma-ray neutron activation analysis, Korean Unexamined Patent Publication No. 10-2010-0119194 (2010.11.09) discloses "a non-destructive inspection method for nuclear fuel rod concentration using a pulsed D-D neutron generator".

Meanwhile, at the time of using a conventional non-destructive inspection apparatus, there are the problems of having to increase the intensity of a neutron source (Cf-252) in order to accomplish high resolution and rapid measurement, having to increase the strength and volume of a shielding in order to block a high radiation dosage rate generated from a neutron source having a high-intensity neutron flux, the neutron source (Cf-252) having to be replaced every three years because its half-life is 2.5 years, it taking a lot of money to maintain this conventional non-destructive inspection apparatus, it being difficult to maintain this conventional non-destructive inspection apparatus, the price of the neutron source (Cf-252) increasing, and the measurement reliability of this conventional non-destructive inspection apparatus decreasing as a result of coefficient compensation depending on the half-life of an isotope (Cf-252). Therefore, in order to solve the above problems, the non-destructive inspection method for nuclear fuel rod concentration using a pulsed D-D neutron generator, disclosed in the Korean Unexamined Patent Publication No. 10-2010-0119194, intends to provide a non-destructive inspection method and apparatus which can measure the concentration of nuclear fissionable materials of a nuclear fuel rod using a pulsed D-D neutron generator and which can rapidly check whether or not a nuclear fuel rod is abnormal.

For this purpose, Korean Unexamined Patent Publication No. 10-2010-0119194 discloses a non-destructive inspection apparatus for inspecting the distribution of concentration of nuclear fuel rods, which includes: a neutron generation unit which intermittently generates neutrons and applies the neutrons to the nuclear fuel rod; and a gamma-ray measurement unit which is disposed under the neutron generation unit with it disposed between the nuclear fuel rods and which measures prompt gamma-rays generated by the nuclear reaction of the nuclear fuel rods.

That is, more concretely, the prompt gamma-ray neutron activation analysis is a method of analyzing the elements in a sample by measuring prompt gamma-rays generated by the nuclear reaction of nuclei and thermal neutrons in the element.

As the neutron radiation source used in such prompt gamma-ray neutron activation analysis, an atomic reactor for research, a radioactive isotope ($^{252}$Cf) or a small neutron generator may be used.

Here, the atomic reactor is advantageous in that it has a high thermal neutron flux of $1.0 \times 10^8 \cdot cm^{-2} \cdot s^{-1}$ or more, but is disadvantageous in that all samples must be moved to the atomic reactor and the size of the sample is limited.

Further, the radioactive isotope is advantageous in that system mobility is easy and in that it is possible to analyze a sample even when the volume of the sample is large, but is disadvantageous in that it is always required to block neutrons because the radioactive isotope spontaneously produces neutrons and in that thermal neutron flux is relatively low.

In contrast, when a femtosecond pulse laser-induced neutron generator is used, a radioactive isotope is advantageous in that system mobility becomes easier and in that it is not required to additionally block neutrons at the time of movement or storage because neutrons are produced only when the laser is being operated.

Further, $^{252}Cf$, which is a radioactive isotope, is disadvantageous in that its neutron flux is subject to being continuously decreased because it has a relatively short half-life (2.6 years). However, a femtosecond pulse laser-induced neutron generator using a D-D nuclear reaction is advantageous in that it can control neutron flux by adjusting the intensity of a laser because it can obtain almost a permanent neutron flux.

Therefore, as described above, when the femtosecond pulse laser-induced neutron generator is used as the neutron radiation source used in the prompt gamma-ray neutron activation analysis, the element in the sample can be non-destructively analyzed. Therefore, it is preferred that a prompt gamma-ray detection apparatus for analyzing chemical materials using femtosecond pulse laser-induced neutrons be used. However, to date, a prompt gamma-ray detection apparatus and method completely satisfying such requirements has not yet been provided.

SUMMARY OF THE INVENTION

Accordingly, the present invention has been devised to solve the above-mentioned problems, and an object of the present invention is to provide a prompt gamma-ray detection apparatus for analyzing chemical materials using femtosecond pulse laser-induced neutrons, whose system mobility is easier than that of a conventional prompt gamma-ray neutron activation analysis using an atomic reactor for research or a radioactive isotope as a neutron radiation source, which does not require that neutrons be additionally blocked at the time of movement or storage because neutrons can be produced only when a laser is operated, and which control neutron flux by adjusting the intensity of a laser because it can obtain almost a permanent neutron flux.

That is, an object of the present invention is to provide a prompt gamma-ray detection apparatus for analyzing chemical materials using femtosecond pulse laser-induced neutrons, which can non-destructively analyze the elements in a sample by measuring prompt gamma-rays generated by the nuclear reaction between the nuclei of a chemical material and thermal neutrons while converting laser-induced neutrons into thermal neutrons using a moderator.

Another object of the present invention is to provide a prompt gamma-ray detection apparatus for analyzing chemical materials using femtosecond pulse laser-induced neutrons, which can advantageously analyze elements, such as hydrogen, nitrogen, phosphorus, sulfur, silicon and the like, which cannot easily be analyzed by conventional non-destructive analysis, such as X-ray fluorescence analysis (XRF), neutron activation analysis (NAA) or the like.

In order to accomplish the above objects, an aspect of the present invention provides a prompt gamma-ray detection apparatus for analyzing chemical materials using femtosecond pulse laser-induced neutrons, which is used in the non-destructive inspection of various materials, such as metals, coal, cement, radioactive materials and the like as well as explosives and chemical materials, and which provides measurement results in the analysis of basic materials, comprising: a femtosecond pulse laser device having beam energy characteristics causing a D-D nuclear fusion reaction; a vacuum chamber for producing neutrons using a femtosecond pulse laser-induced D-D nuclear fusion reaction caused by the femtosecond pulse laser device; a target mount configured to cylindrically mount a plastic target containing deuterium; a rotor for rotating the cylindrical plastic target containing deuterium to continuously generate femtosecond pulse laser-induced neutrons; an outer cover for minimizing the emission of neutrons from the entire outer side of the target mount excluding a laser admission part; a chemical sample mount for mounting a chemical sample that is an object to be measured; a lithium polyethylene port through which specific gamma-rays passes, the specific gamma-rays being generated from chemical components induced from the chemical sample to which thermal neutrons that have passed through the chemical sample mount are applied; a gamma ray measuring unit for detecting the specific gamma-rays that have passed through the lithium polyethylene port; and an extended port configured to enable the gamma ray measuring unit to come as close to a target sample as possible.

Here, the outer cover of the target mount may be used to reflect neutrons, not to absorb neutrons, and may be made of a material that minimizes the emission of neutrons.

Further, the outer cover may be made of a material containing a neutron moderator such that femtosecond pulse laser-induced fast neutrons generated from the target mount are converted into thermal neutrons while they are passing through the chemical sample mount.

Further, the moderator may be made of high-purity high-density polyethylene (pure HDPE).

Further, the chemical sample mount may have a thickness allowing fast neutrons to be converted into thermal neutrons.

Further, the lithium polyethylene port may be made of a material having high neutron absorbance and high gamma-ray transmittance.

Here, the lithium polyethylene port may be provided on an outer side thereof with a high-density polyethylene (HDPE) shield and a lead shield to prevent neutrons and gamma-rays from directly reaching the measuring unit.

Further, the lithium polyethylene port may be made of any one of other neutron shielding materials in addition to HDPE and lead.

Further, the extended port may be made of a metal.

Another aspect of the present invention provides a prompt gamma-ray detection method for analyzing chemical materials using femtosecond pulse laser-induced neutrons, which is used in the nondestructive inspection of various materials, such as metals, coal, cement, radioactive materials and the like as well as explosives and chemical materials, and which provides measurement results in the analysis of basic materials, wherein the method is performed using the prompt gamma-ray detection apparatus.

Still another aspect of the present invention provides a prompt gamma-ray detection apparatus for analyzing chemical materials using femtosecond pulse laser-induced neutrons, which is used in the nondestructive inspection of various materials, such as metals, coal, cement, radioactive materials and the like as well as explosives and chemical materials, and which provides measurement results for the analysis of basic materials, comprising: a chemical sample mount having a thickness allowing fast neutrons to be converted into thermal neutrons and mounting a chemical sample that is a measuring object; a femtosecond pulse laser device having beam energy characteristics causing a D-D nuclear fusion reaction; a vacuum chamber for producing neutrons using a femtosecond pulse laser-induced D-D nuclear fusion reaction caused by the femtosecond pulse laser device; a target mount configured to cylindrically mount a plastic target containing deuterium; an outer cover, which is made of a material that can minimize the emission of neutrons such that the emission of neutrons from the entire outer side of the target mount excluding a laser admission part is minimized, and which is made of a material containing a neutron moderator such that femtosecond pulse laser-induced fast neutrons generated from the target mount are converted into thermal neutrons while they are passing through the chemical sample mount; a rotor for rotating the cylindrical plastic target containing deuterium to continuously generate femtosecond pulse laser-induced neutrons; a lithium polyethylene port, which is made of a material having high neutron absorbance and high gamma-ray transmittance such that thermal neutrons that have passed through the chemical sample mount are applied to the chemical sample, so that the peaks of specific gamma-rays of chemical components induced from each chemical sample are formed, and these specific gamma-rays pass through the lithium polyethylene port, and which is provided on an outer side thereof with a high-density polyethylene (HDPE) shield and a lead shield such that the neutrons and gamma-rays generated from the target do not directly reach the measuring unit; a gamma ray measuring unit for detecting the specific gamma-rays that have passed through the lithium polyethylene port; and an extended port configured to enable the gamma ray measuring unit to come as close as possible to a target sample.

Here, the moderator may be made of high-purity high-density polyethylene (pure HDPE).

Further, the lithium polyethylene port may be made of any neutron shielding material besides HDPE and lead.

Still another aspect of the present invention provides a prompt gamma-ray detection method for analyzing chemical materials using femtosecond pulse laser-induced neutrons, which is used in the nondestructive inspection of various materials, such as metals, coal, cement, radioactive materials and the like as well as explosives and chemical materials, and which provides measurement results in the analysis of basic materials, wherein the method is performed using the prompt gamma-ray detection apparatus.

BRIEF DESCRIPTION OF THE DRAWINGS

The above and other objects, features and advantages of the present invention will be more clearly understood from the following detailed description taken in conjunction with the accompanying drawings, in which.

DESCRIPTION OF THE PREFERRED EMBODIMENTS

Hereinafter, a prompt gamma-ray detection apparatus for analyzing chemical materials using femtosecond pulse laser-induced neutrons according to the present invention will be described in detail with reference to the attached drawings.

Here, these embodiments are set forth to illustrate the present invention, and the scope of the present invention is not limited thereto.

That is, as described later, the prompt gamma-ray detection apparatus of the present invention is configured such that it satisfies the advantages of a conventional gamma-ray detection apparatus, and that it includes a femtosecond pulse laser device, a deuterium mount for a D-D nuclear reaction and a target mount mounting a chemical material and made of the same material as a moderator for reducing fast neutrons into thermal neutrons, and thus it can non-destructively analyze the elements in a sample by measuring prompt gamma-rays generated by the nuclear reaction between the nuclei of a chemical material and thermal neutrons while converting laser-induced fast neutrons into thermal neutrons using a moderator.

More concretely, the prompt gamma-ray detection apparatus of the present invention largely includes a laser device that can induce a D-D nuclear reaction of deuterium, a mount that can mount deuterium, a mount that can mount a chemical sample, and a measuring unit that can measure prompt gamma-rays generated by the nuclear reaction of thermal neutrons and a chemical sample.

Here, a femtosecond pulse laser-induced neutron generator, which is based on a D-D nuclear fusion reaction, generates fast neutrons having a short wavelength of 2.5 MeV. Therefore, thermal neutrons can be obtained by passing the fast neutrons through a moderator such as high-purity polyethylene or the like.

Further, thermal neutrons can be obtained by measuring prompt gamma-rays generated by the nuclear reaction with a chemical sample.

As described above, according to the present invention, qualitative and quantitative analyses can be performed from the spectra of suspected materials using prompt gamma-ray neutron activation analysis which is a method of analyzing the specific gamma peaks of chemical components induced by irradiating samples with neutrons.

Subsequently, hereinafter, preferred embodiments of the prompt gamma-ray detection apparatus for analyzing chemical materials using femtosecond pulse laser-induced neutrons according to the present invention will be described in more detail with reference to the attached drawings.

Figure 1:
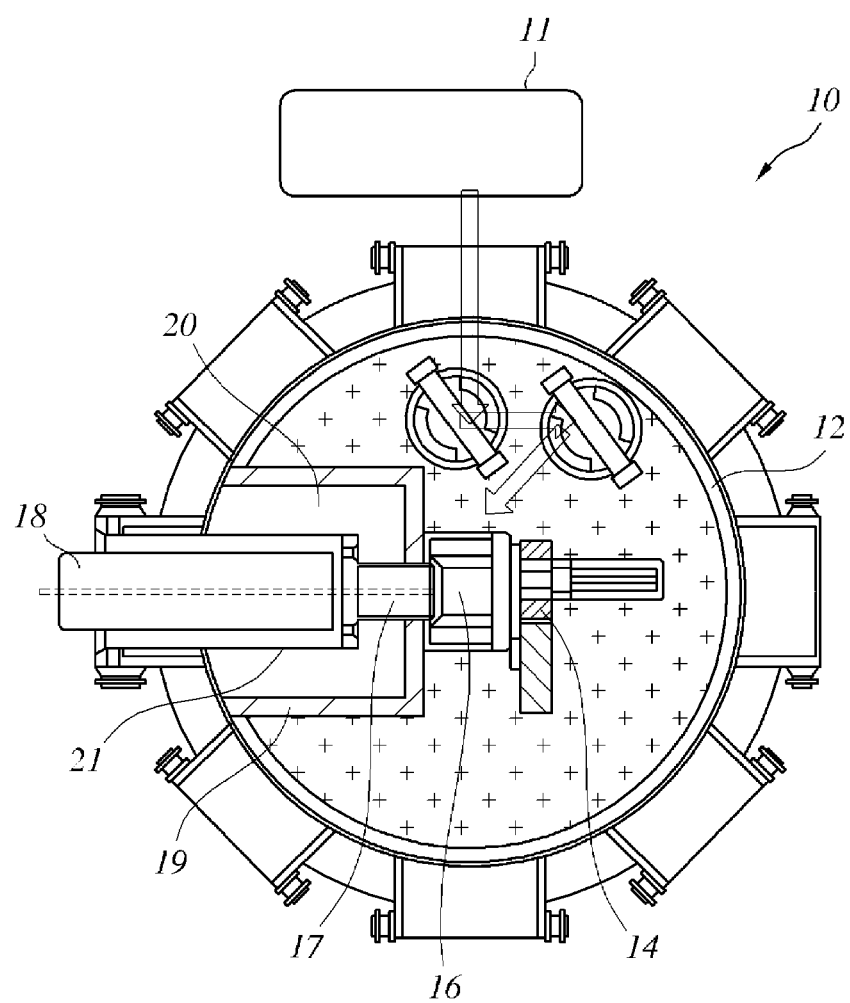
FIG. 1 is a schematic view showing the assembly structure of a prompt gamma-ray detection apparatus for analyzing chemical materials using femtosecond pulse laser-induced neutrons according to the present invention.
Figure 2:
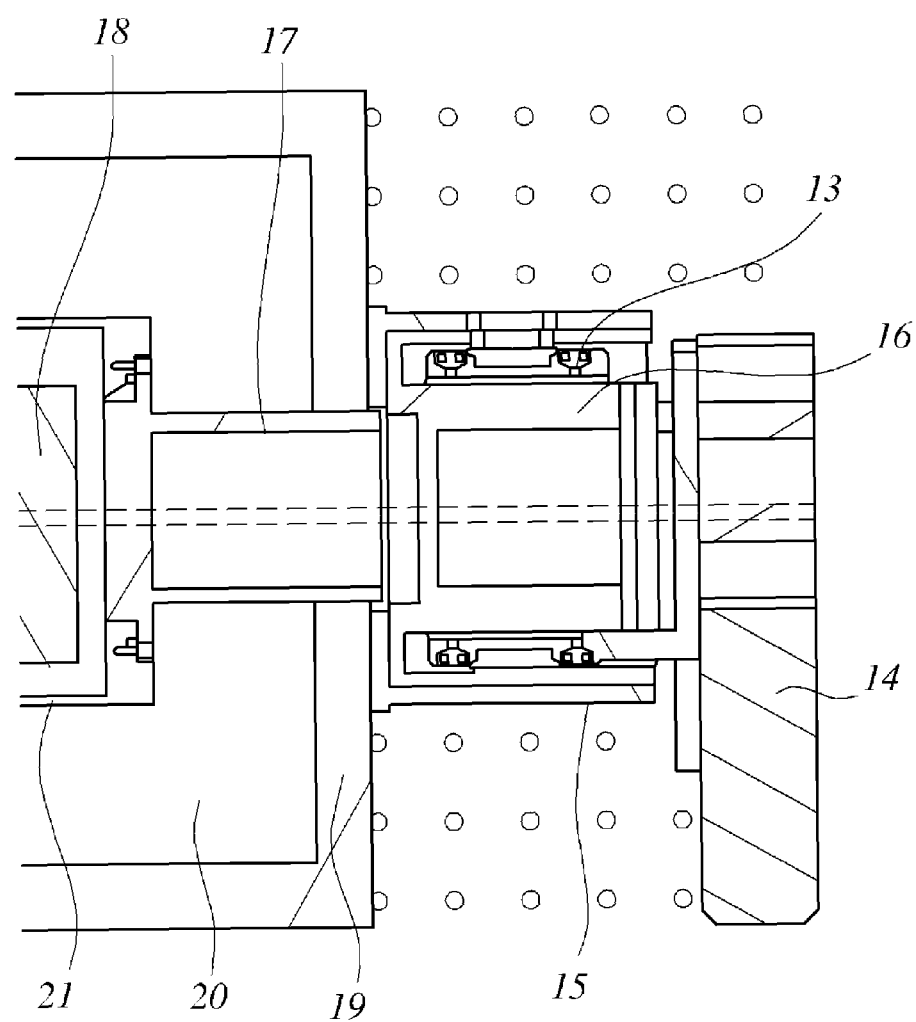
FIG. 2 is an enlarged view of a central part of the assembly structure of the prompt gamma-ray detection apparatus for analyzing chemical materials using femtosecond pulse laser-induced neutrons, shown in FIG. 1, according to the present invention.

FIG. 1 is a schematic view showing the assembly structure of a prompt gamma-ray detection apparatus for analyzing chemical materials using femtosecond pulse laser-induced neutrons according to the present invention; and FIG. 2 is an enlarged view of a central part of the assembly structure of the prompt gamma-ray detection apparatus for analyzing chemical materials using femtosecond pulse laser-induced neutrons, shown in FIG. 1, according to the present invention.

First, as shown in FIG. 1, the prompt gamma-ray detection apparatus 10 for analyzing chemical materials using femtosecond pulse laser-induced neutrons according to the present invention includes a femtosecond pulse laser device 11.

Here, the femtosecond pulse laser device 11 has beam energy characteristics causing a D-D nuclear fusion reaction.

In this case, the prompt gamma-ray detection apparatus 10 includes a vacuum chamber 12 such that neutrons can be produced by a femtosecond pulse laser-induced D-D nuclear fusion reaction.

Further, as shown in FIG. 2, the prompt gamma-ray detection apparatus 10 includes a target mount 13 such that a plastic target containing deuterium is cylindrically mounted.

The cylindrical plastic target containing deuterium is configured such that femtosecond pulse laser-induced neutrons can be continuously generated by the rotation of a rotor 14.

Further, as shown in FIG. 2, the prompt gamma-ray detection apparatus 10 includes an outer cover 15 for minimizing the emission of neutrons from the entire outer side of the target mount 13 excluding its laser admission part.

Here, the outer cover 15 of the target mount 13 is used to reflect neutrons, not to absorb neutrons. Therefore, the outer cover 15 must be made of a material that can minimize the emission of neutrons.

Further, the outer cover 15 must be made of a material containing a neutron moderator such that femtosecond pulse laser-induced fast neutrons generated from the target mount 13 are converted into thermal neutrons while they are passing through a chemical sample mount 16.

Here, the moderator may be made of high-purity high-density polyethylene (pure HDPE), and the chemical sample mount 16 has a thickness allowing fast neutrons to be converted into thermal neutrons.

In this case, the thermal neutrons that have passed through the chemical sample mount 16 are applied to the chemical sample, so that the peaks of specific gamma-rays of chemical components induced from each chemical sample are formed, and these specific gamma-rays reach a gamma-ray measuring unit 18 through a lithium polyethylene port 17.

Here, the raw material of the lithium polyethylene port 17 is not particularly limited, but may be a material having high neutron absorbance and high gamma-ray transmittance.

Moreover, the lithium polyethylene port 17 is provided on the outer side thereof with a high-density polyethylene (HDPE) shield 19 and a lead shield 20. The HDPE shield 19 and the lead shield 20 serve to prevent neutrons and gamma-rays from directly reaching the measuring unit.

The raw materials of the shield are not limited to HDPE and lead as long as they can shield neutrons or gamma-rays.

The prompt gamma-ray detection apparatus 10 may include an extended port 21 such that the measuring unit comes as close to a target sample as possible.

Here, the extended port 21 is made of a metal, but is not limited thereto.

That is, as described above, thermal neutrons that have passed through the chemical sample mount 16 are applied to the chemical sample, so that the peaks of specific gamma-rays of chemical components induced from each chemical sample are formed, and these specific gamma-rays reach the gamma-ray measuring unit 18 through the lithium polyethylene port 17, thereby constituting the prompt gamma-ray detection apparatus 10 for analyzing chemical materials using femtosecond pulse laser-induced neutrons.

Therefore, according to the present invention, there can be provided a prompt gamma-ray detection apparatus 10 for analyzing chemical materials using femtosecond pulse laser-induced neutrons, whose system mobility is easier than that of a conventional prompt gamma-ray neutron activation analysis using an atomic reactor for research or a radioactive isotope as a neutron radiation source, which is not required to additionally block neutrons at the time of movement or storage because neutrons can be produced only when a laser is operated, and which control neutron flux by adjusting the intensity of a laser because it can obtain almost a permanent neutron flux. The prompt gamma-ray detection apparatus 10 can analyze chemical materials using the femtosecond pulse laser-induced neutrons.

Further, according to the present invention, there can be provided a prompt gamma-ray detection apparatus for analyzing chemical materials using femtosecond pulse laser-induced neutrons, which can advantageously analyze elements, such as hydrogen, nitrogen, phosphorus, sulfur, silicon and the like, which cannot be easily analyzed by conventional non-destructive analysis, such as X-ray fluorescence analysis (XRF), neutron activation analysis (NAA) or the like.

Furthermore, according to the present invention, dangerous materials can be easily nondestructively detected from general materials having a composition similar to that of the dangerous materials using the above-mentioned technologies for a short period of time.

As described above, according to the present invention, there is provided a prompt gamma-ray detection apparatus for analyzing chemical materials using femtosecond pulse laser-induced neutrons, which includes a femtosecond pulse laser, a deuterium mount for a D-D nuclear reaction, and a target mount mounting a chemical material and made of the same material as a moderator for reducing fast neutrons into thermal neutrons, and which can non-destructively analyze the elements in a sample by measuring prompt gamma-rays generated by the nuclear reaction between the nuclei of a chemical material and thermal neutrons while converting laser-induced fast neutrons into thermal neutrons using a moderator.

Therefore, according to the present invention, there is provided a prompt gamma-ray detection apparatus for analyzing chemical materials using femtosecond pulse laser-induced neutrons, whose system mobility is easier than that of a conventional prompt gamma-ray neutron activation analysis using an atomic reactor for research or a radioactive isotope as a neutron radiation source, which does not require that neutrons be additionally blocked at the time of movement or storage because neutrons can be produced only when a laser is operated, and which control neutron flux by adjusting the intensity of a laser because it can obtain almost a permanent neutron flux.

Further, according to the present invention, there is provided a prompt gamma-ray detection apparatus for analyzing chemical materials using femtosecond pulse laser-induced neutrons, which can advantageously analyze elements, such as hydrogen, nitrogen, phosphorus, sulfur, silicon and the like, which cannot easily analyzed by conventional non-destructive analysis, such as X-ray fluorescence analysis (XRF), neutron activation analysis (NAA) or the like.

Furthermore, according to the present invention, dangerous materials can be easily nondestructively detected from general materials having a composition similar to that of the dangerous materials using the above-mentioned technologies for a short period of time.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A prompt gamma-ray detection apparatus for analyzing chemical materials using femtosecond pulse laser-induced neutrons, which is used in the nondestructive inspection of the chemical materials, and which provides measurement results for the analysis of basic materials, comprising:

a femtosecond pulse laser device having beam energy characteristics causing a D-D nuclear fusion reaction;

a vacuum chamber for producing neutrons using a femtosecond pulse laser-induced D-D nuclear fusion reaction caused by the femtosecond pulse laser device;

a target mount configured to mount a cylindrical plastic target containing deuterium;
a rotor for rotating the cylindrical plastic target containing deuterium to continuously generate femtosecond pulse laser-induced neutrons;
an outer cover for minimizing the transmission of neutrons from the entire outer side of the target mount excluding a laser admission part;
a chemical sample mount for mounting a chemical sample that is an object to be measured, the chemical sample being positioned coaxially with cylindrical plastic target;
a lithium polyethylene port through which specific gamma-rays pass, the specific gamma-rays being generated from chemical components induced from the chemical sample to which thermal neutrons that have passed through the chemical sample mount are applied;
a gamma ray measuring unit for detecting the specific gamma-rays that have passed through the lithium polyethylene port positioned coaxially with the chemical sample and the lithium polyethylene port; and
an extended port configured to enable the gamma ray measuring unit to come closer to a target sample,
wherein the outer cover of the target mount is comprised of a material that reflects neutrons but does not absorb neutrons, and minimizes the transmission of neutrons, and
wherein the outer cover is made of a material comprising a neutron moderator, wherein the material is capable of converting femtosecond pulse laser-induced fast neutrons generated from the target mount into thermal neutrons while they are passing through the chemical sample mount.

2. The prompt gamma-ray detection apparatus according to claim 1, wherein the moderator is made of high-purity high-density polyethylene (pure HDPE).

3. The prompt gamma-ray detection apparatus according to claim 1, wherein the neutron moderator has a thickness allowing fast neutrons to be converted into thermal neutrons.

4. A prompt gamma-ray detection apparatus for analyzing chemical materials using femtosecond pulse laser-induced neutrons, which is used in the nondestructive inspection of the chemical materials, and which provides measurement results for the analysis of basic materials, comprising:
a chemical sample mount having a thickness allowing fast neutrons to be converted into thermal neutrons and mounting a chemical sample that is an object to be measured, wherein the chemical sample produces peaks of specific gamma rays of chemical components present in the chemical sample when thermal neutrons are applied to the chemical sample;
a femtosecond pulse laser device having beam energy characteristics causing a D-D nuclear fusion reaction;
a vacuum chamber for producing neutrons using a femtosecond pulse laser-induced D-D nuclear fusion reaction caused by the femtosecond pulse laser device;
a target mount configured to mount a cylindrical plastic target containing deuterium, the cylindrical plastic target being positioned coaxially with the chemical sample;
an outer cover surrounding the target mount, which is made of a material that can minimize the transmission of neutrons such that the emission of neutrons from the entire outer side of the target mount excluding a laser admission part is minimized, and which is made of a material containing a neutron moderator, wherein the material is capable of converting femtosecond pulse laser-induced fast neutrons generated from the target mount into thermal neutrons while they are passing through the chemical sample mount;
a rotor for rotating the cylindrical plastic target containing deuterium to continuously generate femtosecond pulse laser-induced neutrons;
a lithium polyethylene port, which is made of a material having high neutron absorbance and high gamma-ray transmittance, the lithium polyethylene port adapted to transmit the specific gamma-rays produced by the chemical sample, and which is provided on an outer side thereof with a high-density polyethylene (HDPE) shield and a lead shield, the HDPE shield and the lead shield surrounding the lithium polyethylene port;
a gamma ray measuring unit positioned coaxially with the chemical sample and the lithium polyethylene port for detecting the specific gamma-rays that have passed through the lithium polyethylene port, the HDPE shield and lead shield provided on the outer side of the lithium polyethylene port configured to prevent the neutrons and gamma rays generated from the target from reaching the gamma ray measuring unit; and
an extended port configured to enable the gamma ray measuring unit to come closer to a target sample.

5. The prompt gamma-ray detection apparatus according to claim 4, wherein the moderator is made of high-purity high-density polyethylene (pure HDPE).

6. A prompt gamma-ray detection method for analyzing chemical materials using femtosecond pulse laser-induced neutrons, which is used in the nondestructive inspection of the chemical materials, and which provides measurement results in the analysis of basic materials
mounting a cylindrical plastic target containing deuterium on a target mount having an outer cover made of a material containing a neutron moderator;
mounting a chemical sample that is an object to be measured on a chemical sample mount coaxially with the cylindrical plastic target;
rotating the cylindrical plastic target by a rotor;
generating femtosecond pulse laser-induced fast neutrons;
converting femtosecond pulse laser-induced fast neutrons generated from the target mount into thermal neutrons while they are passing through the chemical sample mount;
generating specific gamma-rays from chemical components induced from the chemical sample, and passing the specific gamma-rays through a lithium polyethylene port positioned coaxially with the chemical sample; and,
detecting the specific gamma-rays that have passed through the lithium polyethylene port.

* * * * *